United States Patent
Seeck et al.

(10) Patent No.: US 8,767,211 B2
(45) Date of Patent: Jul. 1, 2014

(54) PROCESS FOR THE SELECTIVE DETERMINATION OF OIL MIST OR AEROSOLS

(75) Inventors: Andreas Seeck, Lübeck (DE); Ralf Strothmann, Lübeck (DE); Andreas Mohrmann, Krummesse (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 216 days.

(21) Appl. No.: 13/474,236

(22) Filed: May 17, 2012

(65) Prior Publication Data

US 2013/0107264 A1 May 2, 2013

(30) Foreign Application Priority Data

Oct. 26, 2011 (DE) .......................... 10 2011 117 020

(51) Int. Cl.
*G01N 21/00* (2006.01)
*G01N 21/55* (2014.01)
*G01N 37/00* (2006.01)

(52) U.S. Cl.
USPC ............................ 356/436; 356/445; 73/28.01

(58) Field of Classification Search
None
See application file for complete search history.

(56) References Cited

U.S. PATENT DOCUMENTS

| | | | |
|---|---|---|---|
| 4,321,822 | A | 3/1982 | Marple et al. |
| 6,431,014 | B1 | 8/2002 | Liu et al. |
| 7,712,348 | B2 | 5/2010 | Luebbert et al. |
| 2005/0028616 | A1 | 2/2005 | Marple et al. |
| 2005/0247868 | A1 | 11/2005 | Call et al. |
| 2010/0225918 | A1 | 9/2010 | Aiken et al. |

FOREIGN PATENT DOCUMENTS

| | | |
|---|---|---|
| AU | 2009298228 A1 | 4/2010 |
| DE | 10 2006 023 714 B4 | 4/2008 |
| DE | 10 2008 049 908 A1 | 4/2010 |
| GB | 2438217 A | 11/2007 |
| GB | 2474540 A | 4/2011 |
| WO | 2010/037454 A1 | 4/2010 |

*Primary Examiner* — Gregory J Toatley
*Assistant Examiner* — Amanda Merlino
(74) *Attorney, Agent, or Firm* — McGlew and Tuttle, P.C.

(57) ABSTRACT

An automated analysis method for an impactor used as a measuring transducer for the selective determination of oil mist or aerosols. The process includes the steps of rotating the deflector plate (5) of the measuring transducer (1) about the symmetry axis thereof and of determining the quantity of oil deposited by means of an optical analyzing device from the extinction of a light beam reflected from deflector plate (5) due to the alternation between the background and the pattern produced by the micronozzles (4).

9 Claims, 3 Drawing Sheets

PROCESS FOR THE SELECTIVE DETERMINATION OF OIL MIST OR AEROSOLS

CROSS REFERENCE TO RELATED APPLICATIONS

This application claims the benefit of priority under 35 U.S.C. §119 of German Patent Application DE 10 2011 117 020.4 filed Oct. 26, 2011, the entire contents of which are incorporated herein by reference.

FIELD OF THE INVENTION

The present invention pertains to a process for the selective determination of the quantity of oil mist or aerosols in a gas sample. A device for the selective determination of the quantity of oil mist is known from DE 10 2006 023 714 B4 (and corresponding U.S. Pat. No. 7,712,348 B2). The prior-art measuring transducer is based on the so-called impactor principle, in which an air stream loaded with oil mist or aerosols is suddenly deflected and the deposited oil particles or aerosol particles are collected on a deflector plate. The gas sample to be analyzed now flows through a plurality of micronozzles, which are arranged in a circle and whose diameter is selected to be such that a predetermined test gas flow becomes established. The micronozzles are arranged here at the end of a gas inlet duct, and the deflector plate, at which the oil or aerosol particles are deposited, is located opposite the micronozzles. The quantity of oil or aerosol particles collected during a certain measurement time is an indicator of the oil or aerosol content of the gas sample.

BACKGROUND OF THE INVENTION

The gas sample to be analyzed is usually taken from an overpressure source, e.g., a central compressed air supply unit, in order to make it possible to carry out the gas analysis. The gas inlet duct of the measuring transducer is connected for this to the gas source via a connection plug, and the micronozzles act as nozzles to which supercritical flow is admitted and which limit the flow rate.

The drawback of the prior-art measuring transducer is that analysis depends on the user's perception behavior.

SUMMARY OF THE INVENTION

A basic object of the present invention is to provide an automated analysis method for the selective determination of the quantity of oil mist with the goal of continuous monitoring.

According to the invention, a process is provided for the selective determination of a quantity of oil mist or a quantity of aerosols in a gas sample. The process comprises the steps of providing a device, which has an impactor as a measuring transducer, which has micronozzles for dispensing a predetermined test gas flow and which has a deflector plate downstream of the micronozzles for depositing a non-rotationally symmetrical pattern of aerosol or oil particles on a deflector plate and providing an optical analyzing device. The predetermined test gas flow is dispensed to deposit the non-rotationally symmetrical pattern of aerosol or oil particles on the deflector plate. The deflector plate is rotated relative to the optical analyzing device, about a symmetry axis of the measuring transducer. A quantity of oil deposited is determined by means of the optical analyzing device from an absorbence of a light beam reflected from the deflector plate due to an alternation between gray values of the background and of the pattern.

The pattern may advantageously be a strip pattern, a rectangle pattern, a square pattern or a triangle pattern. A print-mark reader may be used as the optical analyzing device.

According to another aspect of the invention, a device is provided for the selective determination of a quantity of oil mist or a quantity of aerosols in a gas sample. The device comprises an impactor as a measuring transducer, which has micronozzles for dispensing a predetermined test gas flow and which has a deflector plate downstream of the micronozzles. The micronozzles are arranged for depositing a non-rotationally symmetrical pattern of aerosol or oil particles on the deflector plate. An optical analyzing device is provided with a radiation transmitter, which radiates a light beam towards said deflector plate, and a radiation receiver, which receives the reflected light beam. A means is provided for moving the position of the light beam relative to the non-rotationally symmetrical pattern of aerosol or oil particles on a deflector plate. The optical analyzing device determines a quantity of oil deposited based on changes in an intensity of the reflected light beam, from the deflector plate, due to an alternation between regions of the deflector plate with the pattern of aerosol or oil particles and regions of the deflector plate without the pattern of aerosol or oil particles.

The advantage of the process according to the present invention can be seen in that a non-rotationally symmetrical pattern, for example, a straight line, or a plurality of straight lines extending in parallel to one another, which are brought into the beam path of an optical analyzing device by rotation of the impactor about the symmetry axis thereof, is produced on the deflector plate with the measuring transducer known from DE 10 2006 023 714 B4 (and corresponding U.S. Pat. No. 7,712,348 B2). Other suitable patterns may be a strip, a rectangle, a square or a triangle. To generate one or more strips, individual micronozzles, through which the test gas flows, are arranged on a pinhole diaphragm along a straight line. The micronozzles are arranged spaced equidistantly from each other. In case more than one row of holes is provided, another pattern of the micronozzles is selected in the second row of holes in order to expand the measuring range. A solid strip is obtained if the diameters of the oil spots deposited at the micronozzles correspond to the distance between the micronozzles. Commercially available print-mark readers, as they are used to recognize print marks in the graphic arts industry, e.g., packaging machines, are especially well suited for use as optical analyzing devices. These print-mark readers have a sharply delimited light spot and are adjusted such that the light spot is positioned at first at the mark to be recognized and the gray value detected is stored. The background is then detected and stored. An alternation between the gray value of the background and the gray value of the mark develops during rotation of the impactor. The gray value of the mark is obtained from the deposited oil spots. If the gray value of the oil spots exceeds a preset limit value, a signal is sent.

Optical sensors for detecting print marks are described, for example, in DE 10 2008 049 908 A1 (see also English language publication AU 2009298228 A1).

A preferred, average gas flow for the gas sampling is at a value of about 4 L/minute.

The loading of the deflector plate with oil or aerosol particles and the formation of oil spots along one or more straight lines can be observed and subsequently analyzed via a window. Reference is made in this connection to the disclosure of DE 10 2006 023 714 B4, which is part of this application (corresponding U.S. Pat. No. 7,712,348 B2 is hereby incorporated by reference in its entirety).

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 1b is a detail view of the circled region of the measuring transducer of FIG. 1a.

DESCRIPTION OF THE PREFERRED EMBODIMENTS

Figure 1:
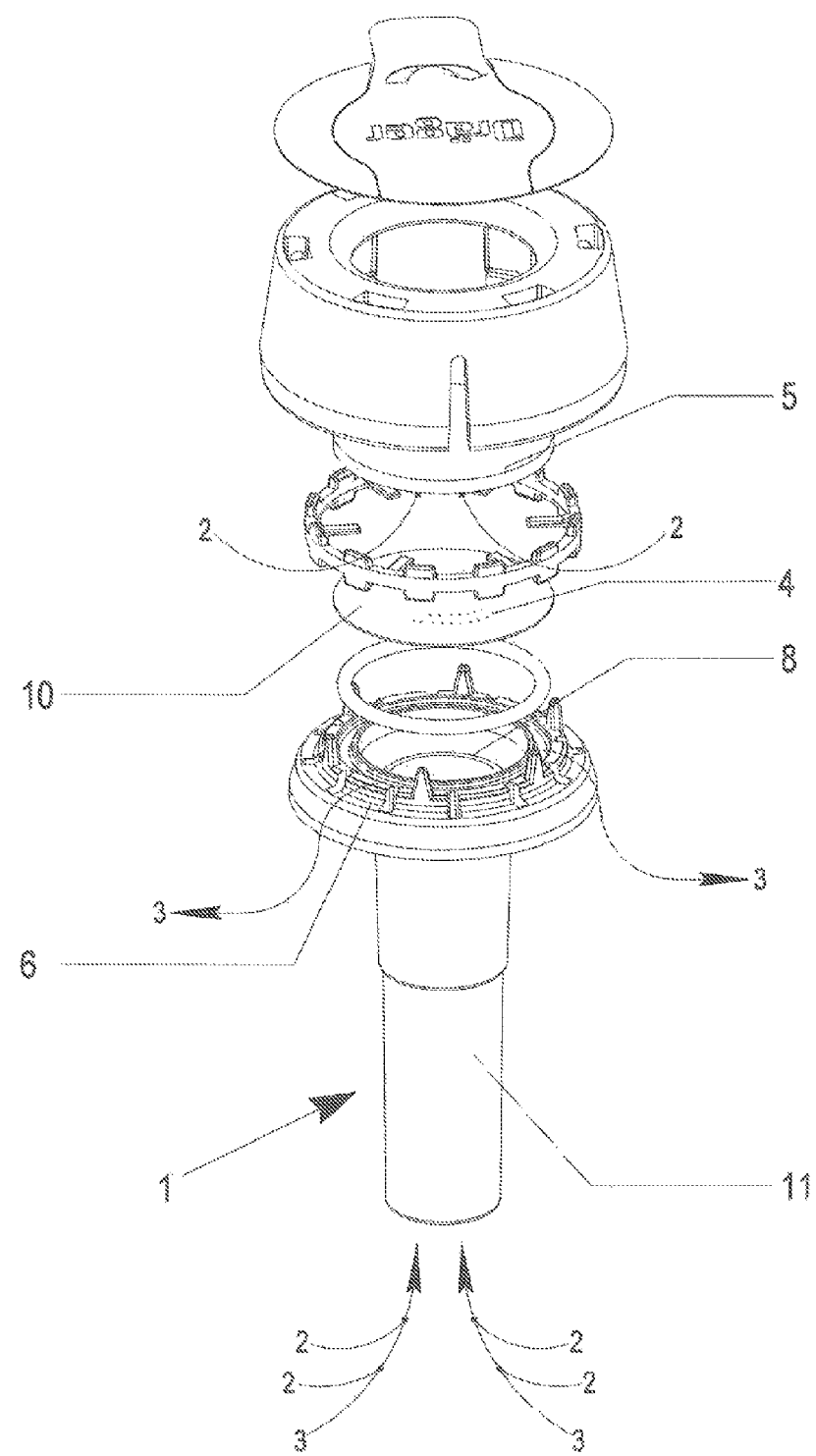
FIG. 1 is a perspective exploded view of a measuring transducer that is part of the device according to the invention.
Figure 1B:
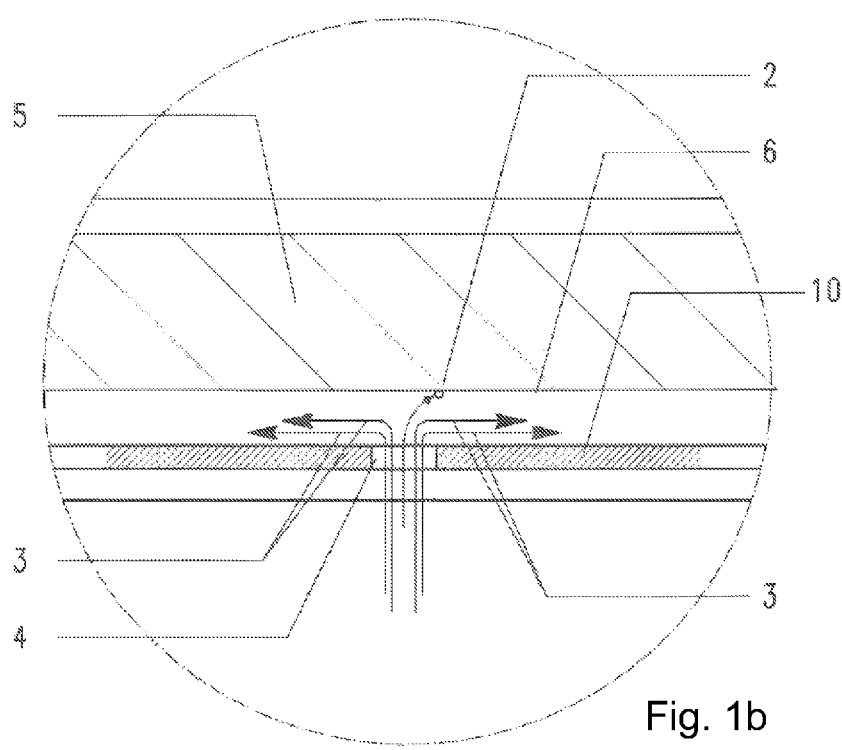
Figure 1A:
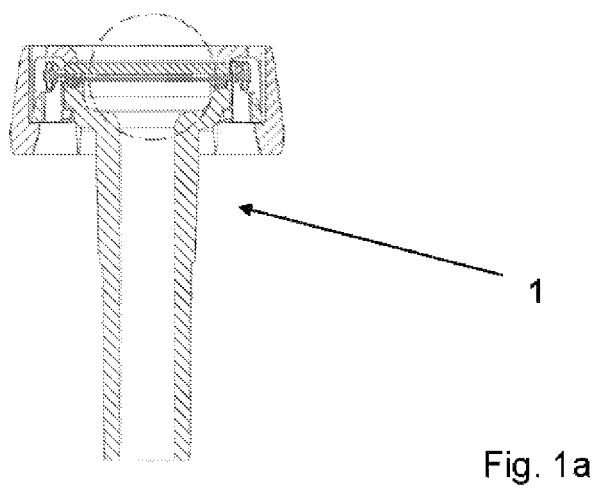
FIG. 1a is a sectional view of the measuring transducer according to FIG. 1.

Referring to the drawings in particular, FIG. 1 schematically shows the design of a measuring transducer 1 for the selective determination of oil mist or aerosols in a perspective view decomposed into its individual parts. The gas 3, which is loaded with oil particles 2 and is arriving from a gas source, not shown in more detail, reaches a pinhole diaphragm 10 with micronozzles 4 in a housing 11 via a gas inlet duct 8 and is deflected on the inside 6 of a transparent deflector plate 5 at right angles to the direction of inflow. Based on the abruptly changing flow direction, the oil particles 2 cannot follow the flow any longer and are deposited on the inside 6 of deflector plate 5. FIG. 1a shows a detail X of the measuring transducer 1 according to FIG. 1. Only one micronozzle 4 is shown in FIG. 1 for the sake of greater clarity. The diameter of an oil spot deposited in the area of micronozzle 4 is perceptible via a window 7. Measuring transducer 1 has a symmetry axis 9.

Figure 2:
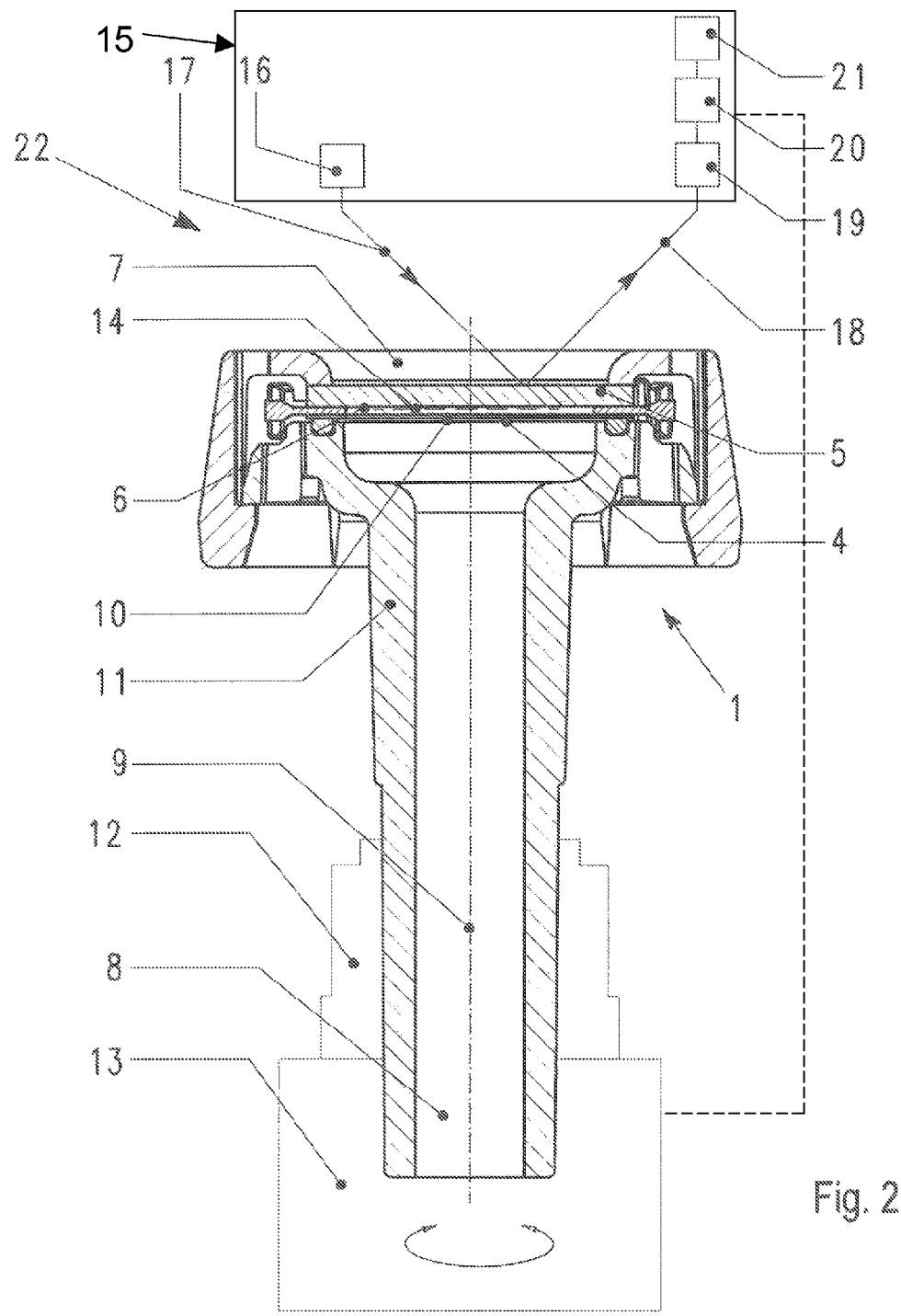
FIG. 2 is a schematic partially sectional view showing a measuring device according to the present invention.

FIG. 2 schematically illustrates the design of the measuring device 22 according to the present invention. Housing 11 has, opposite the deflector plate 5, a pinhole diaphragm 10 with micronozzles 4, which are arranged along a straight line and at equally spaced locations from one another. A pattern 14 of oil spots, which are located next to each other and extend along a straight line, is produced on the deflector plate 5 by the micronozzles 4 arranged on the pinhole diaphragm 10. Depending on the quantity of oil aerosol deposited and depending on the distance between the micronozzles 4, confluent oil spots, which form a solid straight line or a strip, are formed on deflector plate 5.

Housing 11 of the measuring transducer 1 is accommodated in a mount 12 with a motor 13 rotating the housing 11. Housing 11 rotates about the symmetry axis 9. The gas to be measured, which enters via the gas inlet duct 8, flows through the micronozzles 4 and generates on the inside 6 of the deflector plate 5 a pattern 14 of individual oil spots, which merge into one another. An optical analyzing device 15 arranged in the area of window 7 of the deflector plate 5 comprises a radiation transmitter 16, which radiates a light beam 17 towards the deflector plate 5, and a radiation receiver 19, which receives the reflected light beam 18. A limit value transducer 20 determines changes in the intensity of the reflected light beam 18 and generates a signal at a display unit 21 when a limit value is exceeded. Different gray values, which arise from the alternation of reflections of the background and pattern 14, are detected by the optical analyzing device 15 due to the rotation of strip 14. The gray value of pattern 14 is proportional to the quantity of oil deposited, as a result of which a quantitative analysis is possible by comparison with the gray value of the background.

The measuring device 22 according to the embodiment of FIG. 2 provides a means for moving the position of the light beam 17 relative to the non-rotationally symmetrical pattern 14 of aerosol or oil particles on the deflector plate 5 in the form of the motor 13 in cooperation with the transducer 1 accommodated in the mount 12 with the motor 13 rotating the housing 11. As an alternative, the optical analyzing device 15 may be rotated about the symmetry axis 9 or other structure may be employed that moves the position of the light beam 17 relative to the non-rotationally symmetrical pattern 14.

The limit value transducer 20 may include or be part of a processor system, of the optical analyzing device 15, that determines the quantity of oil deposited based on changes in the intensity of the reflected light beam 18 from the deflector plate 5 due to an alternation between regions of the deflector plate 5 with the pattern of aerosol or oil particles 2 and regions of the deflector plate 5 without the pattern of aerosol or oil particles 2. Such a processor may also control the rotation function or other change in the position of the light beam 17 or other changes in relative position between the optical analyzing device 15 and the pattern 14.

While specific embodiments of the invention have been shown and described in detail to illustrate the application of the principles of the invention, it will be understood that the invention may be embodied otherwise without departing from such principles.

What is claimed is:

1. A process for the selective determination of a quantity of oil mist or a quantity of aerosols in a gas sample, the process comprising the steps of:

providing a device, which has an impactor as a measuring transducer, which has micronozzles for dispensing a predetermined test gas flow and which has a deflector plate downstream of the micronozzles for depositing a non-rotationally symmetrical pattern of aerosol or oil particles on said deflector plate;

providing an optical analyzing device;

dispensing the predetermined test gas flow to deposit the non-rotationally symmetrical pattern of aerosol or oil particles on the deflector plate;

rotating the deflector plate relative to the optical analyzing device, about a symmetry axis of the measuring transducer;

determining a quantity of oil deposited by means of the optical analyzing device from an absorbence of a light beam reflected from the deflector plate due to an alternation between gray values of the background and of the pattern.

2. A process in accordance with claim 1, wherein the pattern is a strip pattern, a rectangle pattern, a square pattern or a triangle pattern.

3. A process in accordance with claim 1, wherein a printmark reader is used as the optical analyzing device.

4. A process for the selective determination of a quantity of oil mist or a quantity of aerosols in a gas sample, the process comprising the steps of:

providing a device, which has an impactor as a measuring transducer, which has micronozzles for dispensing a predetermined test gas flow and which has a deflector plate downstream of the micronozzles;

arranging the micronozzles for depositing a non-rotationally symmetrical pattern of aerosol or oil particles on the deflector plate;

providing an optical analyzing device with a radiation transmitter, which radiates a light beam towards said deflector plate, and a radiation receiver, which receives the reflected light beam;

dispensing the predetermined test gas flow to deposit the non-rotationally symmetrical pattern of aerosol or oil particles on the deflector plate;

moving the position of the light beam relative to the non-rotationally symmetrical pattern of aerosol or oil particles on the deflector plate;

determining a quantity of oil deposited by means of the optical analyzing device based on changes in the intensity of the reflected light beam from the deflector plate due to an alternation between regions of the deflector plate with the pattern of aerosol or oil particles and regions of the deflector plate without the pattern of aerosol or oil particles.

5. A process in accordance with claim 4, wherein the pattern is a strip pattern, a rectangle pattern, a square pattern or a triangle pattern.

6. A process in accordance with claim 4, wherein a printmark reader is used as the optical analyzing device.

7. A device for the selective determination of a quantity of oil mist or a quantity of aerosols in a gas sample, the device comprising:

an impactor as a measuring transducer, which has micronozzles for dispensing a predetermined test gas flow and which has a deflector plate downstream of the micronozzles, the micronozzles being arranged for depositing a non-rotationally symmetrical pattern of aerosol or oil particles on the deflector plate;

an optical analyzing device with a radiation transmitter, which radiates a light beam towards said deflector plate, and a radiation receiver, which receives the reflected light beam; and a means for moving the position of the light beam relative to the non-rotationally symmetrical pattern of aerosol or oil particles on the deflector plate, wherein the optical analyzing device determines a quantity of oil deposited based on changes in an intensity of the reflected light beam, from the deflector plate, due to an alternation between regions of the deflector plate with the pattern of aerosol or oil particles and regions of the deflector plate without the pattern of aerosol or oil particles.

8. A device in accordance with claim 7, wherein the pattern is a strip pattern, a rectangle pattern, a square pattern or a triangle pattern.

9. A device in accordance with claim 7, wherein a printmark reader is used as the optical analyzing device.

* * * * *